United States Patent
Garcia (10) Patent No.: US 10,252,025 B2
(45) Date of Patent: Apr. 9, 2019

(54) URINARY PROSTHESES

(71) Applicant: Justin Garcia, Bothell, WA (US)

(72) Inventor: Justin Garcia, Bothell, WA (US)

(*) Notice: Subject to any disclaimer, the term of this patent is extended or adjusted under 35 U.S.C. 154(b) by 8 days.

(21) Appl. No.: 15/286,414

(22) Filed: Oct. 5, 2016

(65) Prior Publication Data

US 2017/0095323 A1   Apr. 6, 2017

Related U.S. Application Data

(60) Provisional application No. 62/237,343, filed on Oct. 5, 2015.

(51) Int. Cl.
*A61M 25/00* (2006.01)
*A61M 25/01* (2006.01)
*A61M 25/04* (2006.01)
*A61F 2/04* (2013.01)

(52) U.S. Cl.
CPC .... *A61M 25/0017* (2013.01); *A61M 25/0127* (2013.01); *A61M 25/04* (2013.01); *A61F 2002/047* (2013.01); *A61F 2210/009* (2013.01); *A61F 2220/0008* (2013.01); *A61F 2240/002* (2013.01); *A61F 2250/0002* (2013.01); *A61F 2250/006* (2013.01); *A61F 2250/0096* (2013.01); *A61M 2025/0046* (2013.01); *A61M 2025/0073* (2013.01); *A61M 2205/3334* (2013.01)

(58) Field of Classification Search
CPC .................. A61F 2/04; A61F 2210/009; A61F 2002/047; A61F 2250/0096; A61F 2250/006; A61F 2240/002; A61F 2220/0008; A61M 25/0017; A61M 25/0127; A61M 25/04; A61M 2025/0073; A61M 2025/0046; A61M 2205/3334
See application file for complete search history.

(56) References Cited

U.S. PATENT DOCUMENTS

| 3,575,158 | A | * | 4/1971 | Summers | A61F 2/0036 |
| | | | | | 128/DIG. 25 |
| 5,762,599 | A | * | 6/1998 | Sohn | A61F 2/0018 |
| | | | | | 417/420 |
| 2005/0267566 | A1 | * | 12/2005 | Rioux | A61M 25/04 |
| | | | | | 623/1.28 |
| 2005/0283235 | A1 | * | 12/2005 | Kugler | A61B 17/12009 |
| | | | | | 623/14.13 |

(Continued)

OTHER PUBLICATIONS

Inline Fan, URL=http://www.suncourt.com/product/DB200C, Download date Dec. 7, 2016. (4 pages) (believed to be publicly available prior to the filing of the present application).

(Continued)

*Primary Examiner* — David Isabella
*Assistant Examiner* — Rokhaya Diop
(74) *Attorney, Agent, or Firm* — Seed IP Law Group LLP (57) ABSTRACT

A urinary prosthesis can include an elongate tube that can extend from outside a patient's body, through the patient's urethra, and into the patient's bladder. A funnel can be coupled to a terminal end portion of the elongate tube, and can be positioned inside the patient's bladder so that a surface of the funnel contacts tissue within the patient's bladder surrounding the patient's urethra across a full 360° contact profile.

9 Claims, 9 Drawing Sheets

(56) References Cited

U.S. PATENT DOCUMENTS

2010/0130815 A1* 5/2010 Gross ................. A61F 2/92
600/30

OTHER PUBLICATIONS

Mining Trommel, URL=http://www.clasf.co.za/mobile-gold-trommel-in-louis-trichardt-1392918, Download date Dec. 7, 2016. (4 pages) (believed to be publicly available prior to the filing of the present application).
10 Piece Knuckle Set, URL=http://www.hoses.co.uk/adaptors-and-fittings/lube-cool/10-piece-knuckle-set-lube-cool-system, Download Date Dec. 7, 2016. (3 pages) (believed to be publicly available prior to the filing of the present application).
Knuckle Joint, URL=http://circuit-hydraulics.co.uk/ProductDetail/5/295/2055/4729, Download date Dec. 7, 2016. (1 page) (publicly available as early as Sep. 15, 2012).
Vesiflo, URL=http://vesiflo.com, Archived by the Internet Archive on Sep. 18, 2015; Accessed via the Wayback Machine on Jan. 11, 2017. (7 pages).
Vesiflo Newscast, URL=http://www.king5.com/news/health/under-active-bladder/216566895, Download Date Dec. 7, 2016. (2 pages) (dated May 26, 2016).

\* cited by examiner

URINARY PROSTHESES

BACKGROUND

Technical Field

The present disclosure relates to prostheses and catheters generally, and to prostheses and catheters for use in a patient's urinary tract in particular.

Description of the Related Art

Prostheses and catheters have been developed for use in a patient's urinary tract, but prior devices suffer from various drawbacks, including causing excessive patient discomfort, which limit their use.

BRIEF SUMMARY

A urinary prosthesis can include an elongate tube that can extend from outside a patient's body, through the patient's urethra, and into the patient's bladder. A funnel can be coupled to a terminal end portion of the elongate tube, and can be positioned inside the patient's bladder so that a surface of the funnel contacts tissue within the patient's bladder surrounding the patient's urethra across a full 360° contact profile. A tubular assembly of a urinary prosthesis can include a plurality of rigid links that are coupled to one another so that the tubular assembly as a whole is flexible. Such a tubular assembly can also include plural magnetic components that can be remotely actuated to rotate within the tubular assembly.

A urinary prosthesis may be summarized as comprising: an elongate flexible tube; a flexible funnel including a surface coupled to the elongate flexible tube, the surface having a single circular edge at its outer periphery to provide a 360° contact profile for contacting native bladder tissues; and a flexible stabilizer coupled to the flexible funnel and extending laterally away from the flexible funnel.

The urinary prosthesis may further comprise a plurality of flexible stabilizers coupled to the flexible funnel and extending laterally away from the flexible funnel, the plurality of flexible stabilizers including the flexible stabilizer, and the plurality of flexible stabilizers spaced equidistantly apart from one another around the flexible funnel. Each of the plurality of flexible stabilizers may be canted and have a consistent cant. The surface of the flexible funnel coupled to the elongate flexible tube may be connected to the elongate flexible tube at an angle between 90° and 135°. The angle may be based on an individual patient's anatomy. A portion of the surface of the flexible funnel coupled to the elongate flexible tube may have a radius of curvature between 1 mm and 10 mm. The radius of curvature is based on an individual patient's anatomy. The funnel may comprise a first material, the elongate flexible tube may comprise a second material, and the first material may be denser than the second material, or the second material may be denser than the first material.

A urinary prosthesis may be summarized as comprising: an elongate flexible tube having a central longitudinal axis, the elongate flexible tube including: an outer sheath; a plurality of individual links positioned within the outer sheath, each of the individual links including an annular, rigid body, a first one of the links coupled to a second one of the links so that the first one of the links is rotatable about an axis transverse to the central longitudinal axis with respect to the second one of the links; and a first hollow, cylindrical body that is positioned within the first one of the links and that is rotatable with respect to the first one of the links.

The first individual link may include a first end portion that is tapered, the second individual link may include a second end portion that has a constriction, and the first end portion may be seated on and within the constriction of the second end portion. A curvature of the first end portion may correspond to a curvature of the second end portion so that the first end portion is sealed to the second end portion. The first hollow cylindrical body may include a first helical ridge extending inwardly from an inner surface of the first hollow cylindrical body and a second helical ridge extending inwardly from the inner surface of the first hollow cylindrical body. The first helical ridge may include a first curved surface having a varying radius of curvature and the second helical ridge may include a second curved surface having a varying radius of curvature. The first and second helical ridges may be magnetic or ferromagnetic.

The urinary prosthesis may further comprise a respective hollow, cylindrical body positioned within and rotatable with respect to each of the plurality of individual links. The urinary prosthesis may further comprise a second hollow, cylindrical body that is positioned within the second one of the links and that is rotatable with respect to the second one of the links. The first hollow cylindrical body may be independently rotatable with respect to the second hollow cylindrical body. The first hollow cylindrical body may be constrained to rotate in unison with the second hollow cylindrical body. The urinary prosthesis may further comprise a lubricant positioned between an inner surface of the first one of the links and an outer surface of the first hollow, cylindrical body.

BRIEF DESCRIPTION OF THE SEVERAL VIEWS OF THE DRAWINGS

In the drawings, sizes and relative positions of elements are not necessarily drawn to scale.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with the prostheses for the urinary tract and catheters or other delivery devices or techniques have not been shown or described in detail to avoid unnecessarily obscuring descriptions of the embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
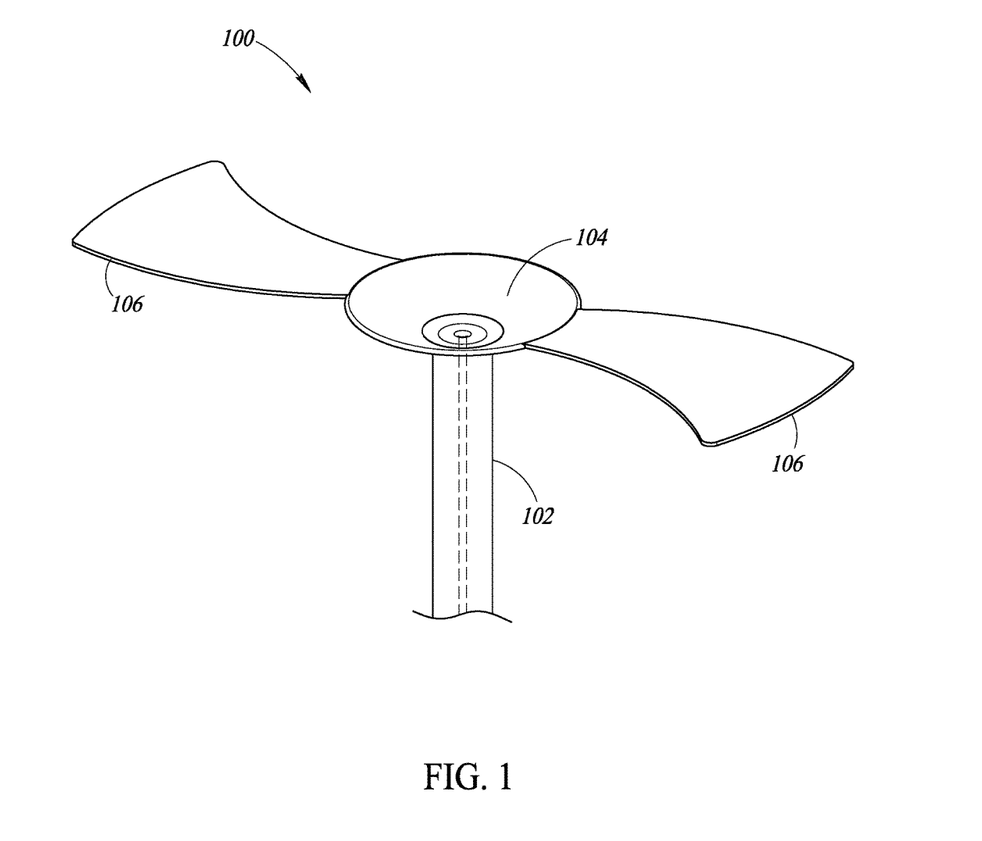
FIG. 1 illustrates a urinary prosthesis according to one embodiment.
Figure 2:
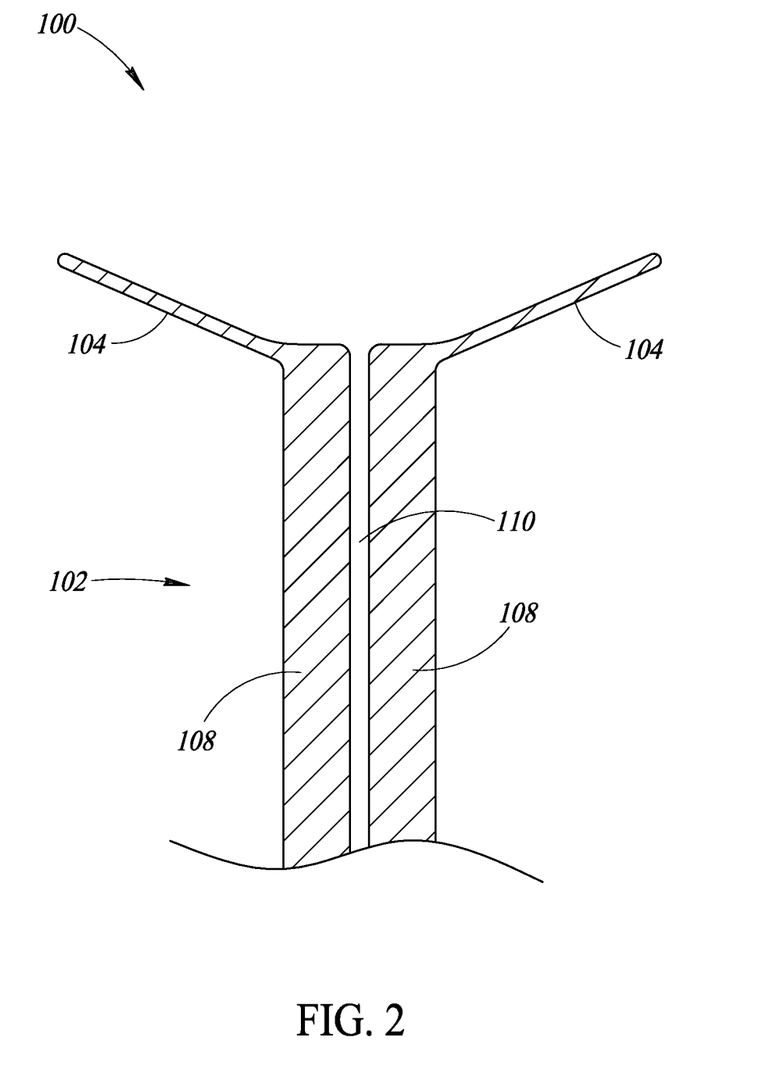
FIG. 2 illustrates a cross-sectional view of the urinary prosthesis of FIG. 1.

FIG. 1 illustrates a urinary prosthesis or a urinary catheter 100, according to one embodiment. Urinary prosthesis 100 includes an elongate flexible tube 102, a flexible funnel or nest 104, and two flexible petals, wings, or stabilizers 106 extending laterally away from the funnel 104. FIG. 2 illustrates a cross-sectional view of the urinary prosthesis 100 along a plane such that the stabilizers 106 are not visible. As shown in FIG. 2, the tube 102 can include an outer flexible shell 108 surrounding an inner flexible conduit 110. The conduit 110 can be formed as an opening through the shell 108, or can include a separate piece of tubular material extending through the shell 108. The funnel 104 can funnel fluids (e.g., urine) or other materials (e.g., kidney stones or other mineral build-up) toward the inner flexible conduit 110, and can either channel and guide them into and through the flexible conduit 110, or can block or capture them before they pass through the flexible conduit 110. The shell 108 of the tube 102, the funnel 104, and the stabilizers 106 can comprise the same material as one another and can be integrally formed with one another.

Figure 3:
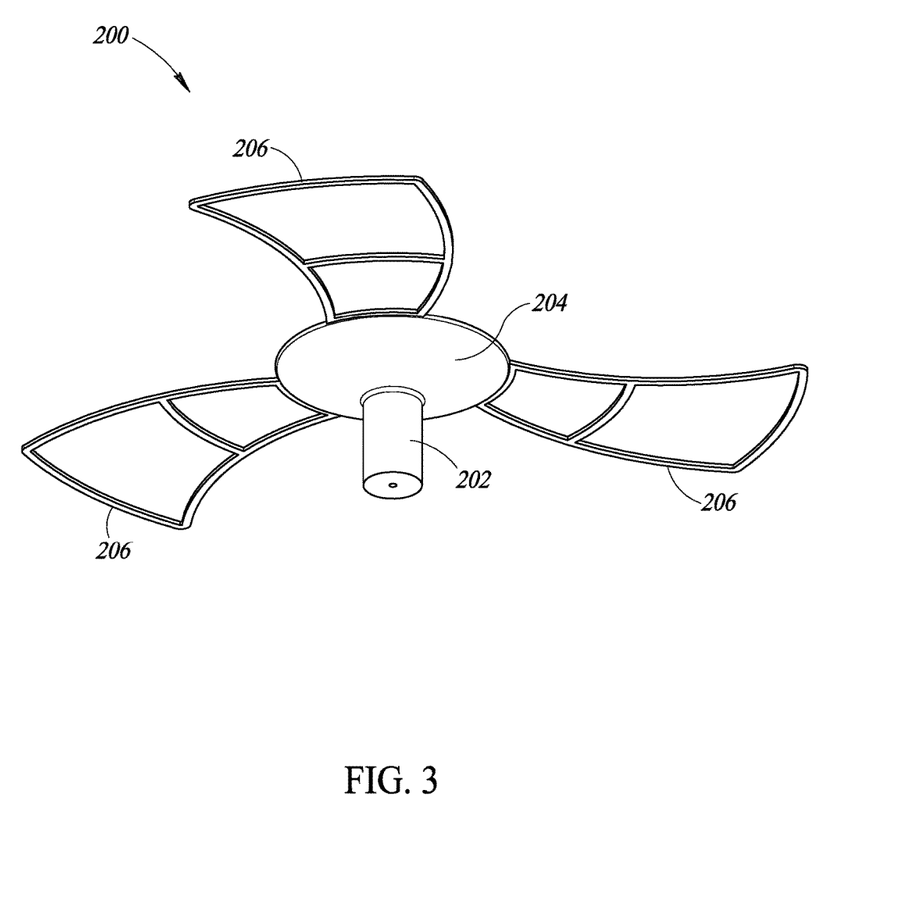
FIG. 3 illustrates a urinary prosthesis according to another embodiment.

FIG. 3 illustrates a urinary prosthesis or urinary catheter 200 according to another embodiment, similar to urinary prosthesis 100, that includes a tube 202, a funnel 204, and three stabilizers 206 coupled to the funnel 204. The stabilizers 206 differ from the stabilizers 106 in that, whereas the stabilizers 106 comprise a solid sheet of flexible material, the stabilizers 206 include a network of shafts or segments of the flexible material, which can be extruded and interconnected at a plurality of ultra-low-resistance flexible joints. The funnels 104 and 204 are illustrated as including a solid sheet of flexible material, although the funnels 104 and 204 in alternative implementations can also include a network of interconnected shafts or segments of a flexible material. The example prosthesis 100 of FIG. 1 includes two stabilizers and the example prosthesis 200 of FIG. 3 includes three stabilizers, but in practice, any suitable number of stabilizers can be used. In various implementations, the stabilizers of a prosthesis can include solid sheets of flexible material, interconnected shafts or segments of the flexible material, or any combination thereof.

Figure 4:
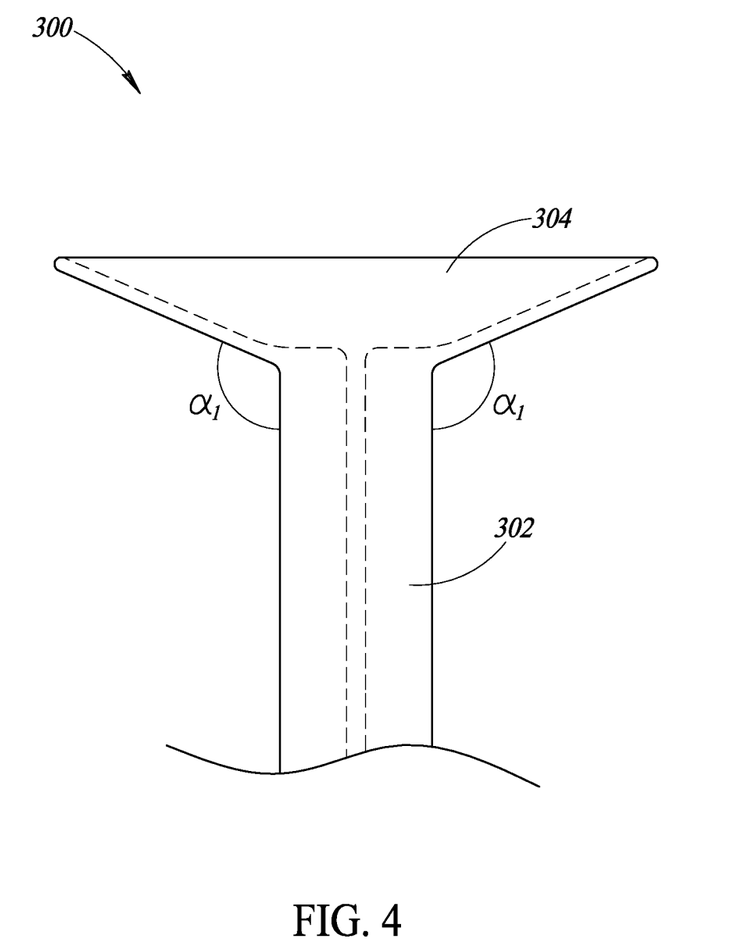
FIG. 4 illustrates a urinary prosthesis, according to another embodiment, having a first component coupled to a second component at a first angular dimension.
Figure 5:
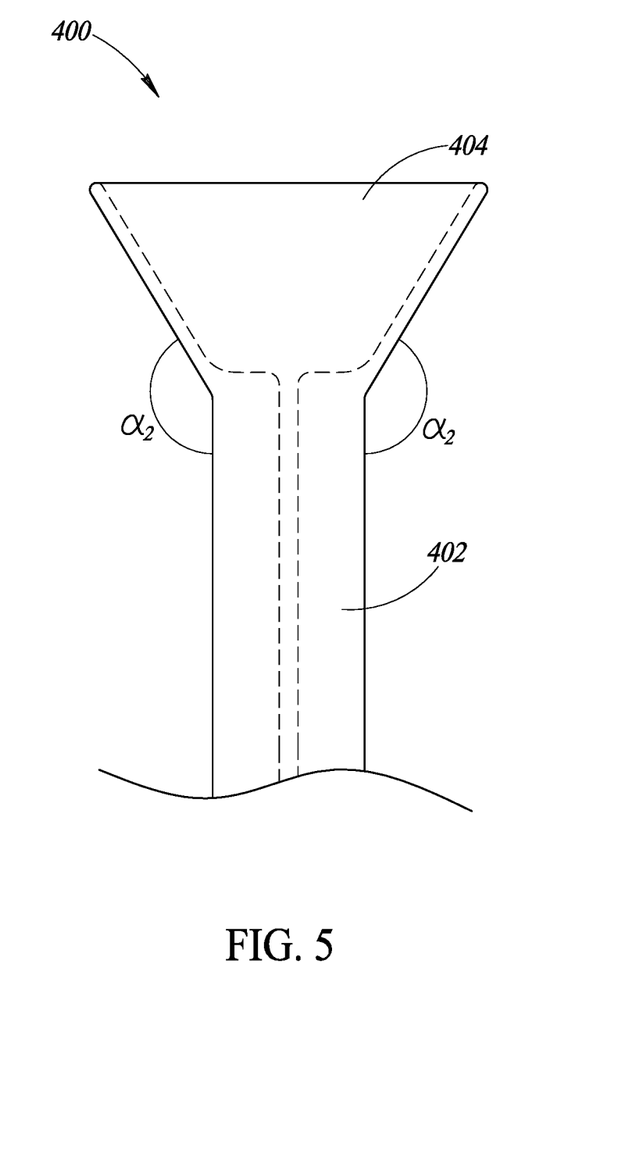
FIG. 5 illustrates a urinary prosthesis, according to another embodiment, having a first component coupled to a second component at a second angular dimension.

FIG. 4 illustrates a urinary prosthesis or urinary catheter 300 according to another embodiment that includes a tube 302 connected to a funnel 304 at a first angle $\alpha_1$. FIG. 5 illustrates a urinary prosthesis or urinary catheter 400 according to another embodiment that includes a tube 402 connected to a funnel 404 at a second angle $\alpha_2$, wherein $\alpha_2 > \alpha_1$. In various implementations, $\alpha_2$ and $\alpha_1$ can be any angle, however, particularly suitable angles are within the range of about 90° to about 180°, and even more particularly, between 90° and 135°.

Figure 6:
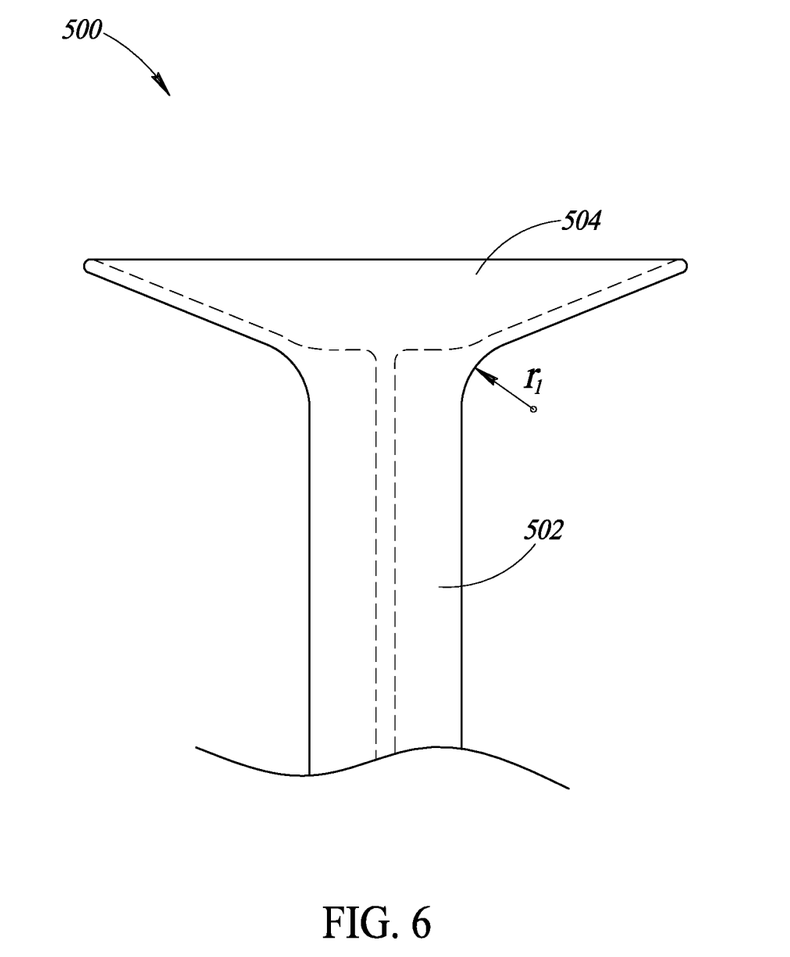
FIG. 6 illustrates a urinary prosthesis, according to another embodiment, including a component having a first radius of curvature.
Figure 7:
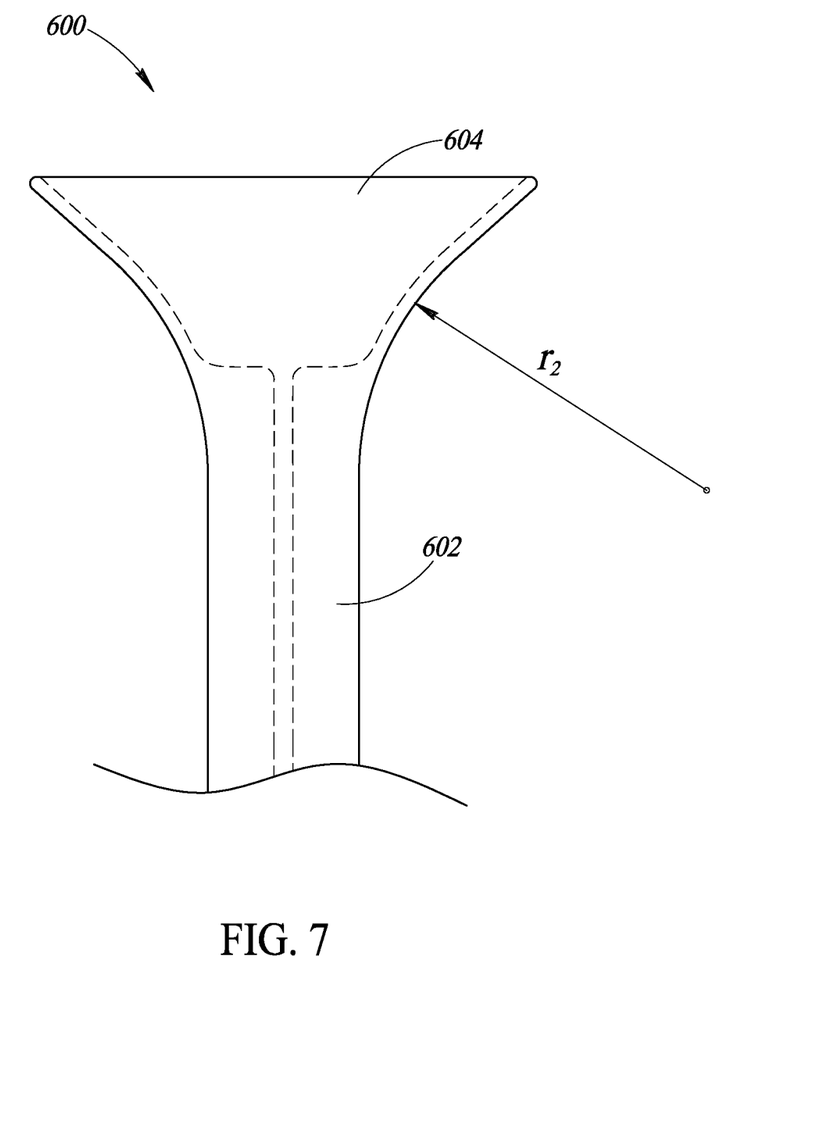
FIG. 7 illustrates a urinary prosthesis, according to another embodiment, including a component having a second radius of curvature.

FIG. 6 illustrates a urinary prosthesis or urinary catheter 500 according to another embodiment that includes a tube 502 connected to a funnel 504 having a first radius of curvature between a location where the funnel 504 meets the tube 502 and a non-curved or linear portion of the funnel 504 of $r_1$. FIG. 7 illustrates a urinary prosthesis or urinary catheter 600 according to another embodiment that includes a tube 602 connected to a funnel 604 having a second radius of curvature between a location where the funnel 604 meets the tube 602 and a non-curved or linear portion of the funnel 604 of $r_2$, wherein $r_2 > r_1$. In various implementations, $r_2$ and $r_1$ can range from at least about 1 mm up to about 10 mm.

A shell (e.g., shell 108), a funnel (e.g., funnel 104), and stabilizers (e.g., stabilizers 106) can include a relatively soft, flexible, conformable, pliable, compliant, and/or resilient material, such as any suitable plastic, elastomer, rubber, gel, or other material. These components can therefore conform to the shapes of the native tissues within a patient's body. For example, a portion of the shell 108 adjacent to the funnel 104 can comprise a memory gel or a low-impact and super-pliable material. As another example, the shell 108 can extend through a patient's urethral sphincters and can conform to the shape of the patient's urethral sphincters to allow the urethral sphincters to partially close around the tube 102 so they remain in a more relaxed (and comfortable) state than otherwise.

As another example, with reference to FIG. 1, the surface of the funnel 104 closest to the tube 102 can be designed to rest against the interior of a patient's bladder adjacent to the patient's internal urethral opening. This surface can include a minimal number of edges and corners that can cause patient discomfort. For example, this surface can include a single circular edge at its outer periphery and can bear against the native tissues of the interior of the patient's bladder across a full 360° contact profile, thereby evenly distributing forces and stresses from the prosthesis 100 into the patient's tissues across a larger surface area. Once positioned within a patient's urethra, prostheses often encounter various forces urging them out of the patient's body through the urethra, such as fluid pressure within the bladder, the human body's natural tendency to expel foreign objects, and forces resulting from movement of the patient. Spreading these forces out over a larger surface area can increase patient comfort by reducing stress concentrations. Further, because the funnel 104 bears against the patient's bladder across a full 360° contact profile, it can also seal the patient's bladder at the internal urethral opening, thereby reducing the need to force the patient's sphincters open to prevent leakage, thereby ultimately improving patient comfort and increasing the amount of time a prosthesis can remain in the patient's body, for example, up to at least 30 days.

Stabilizers (e.g., stabilizers 106) can help to hold the prosthesis 100 and the funnel 104 at a specific location within a patient's bladder, and can form or include drainage pathways, channels, grooves, guides, or ridges, to direct, block, route, or divert the flow of fluid such as urine within the patient's bladder, such as toward the funnel 104 and the tube 102. The inner conduit 110 can include a piece of flexible tubular material extending through the shell 108 that provides sufficient rigidity to ensure that the conduit 110 remains open when the tube 102 extends through a patient's urethral sphincters to allow urine to drain out of the patient's bladder. That is, the inner conduit 110 can include a piece of tubular material that prevents collapse of the inner conduit 110 when the prosthesis 100 is inserted through a patient's urethra.

A method of using any of the prostheses described herein can include measuring a patient's anatomy to select an appropriately dimensioned prosthesis. Once the measurements have been taken, a prosthesis can be custom-manufactured to match the patient's body or a prosthesis can be selected from a plurality of pre-manufactured prostheses to approximate the patient's anatomical dimensions as closely as possible. For example, a prosthesis can be manufactured or selected to include a tube having a length and a diameter, and to include an angle α or a radius of curvature r, as described above, to match a patient's anatomy. The prostheses described herein can be packaged in surgical-grade sterile packaging.

The method can also include packaging a prosthesis within an introducer such as a syringe by folding the funnel and stabilizers of the prosthesis together to extend in front of the tube. The syringe, with the prosthesis packaged therein, can be inserted through a patient's urethra so that a distal end thereof is within the patient's bladder and so that the tube extends from outside of the patient's body, through the patient's anterior and posterior urethral sphincters, and into the patient's bladder. A plunger of the syringe can then be pushed, causing the stabilizers and the funnel of the prosthesis to open and deploy within the patient's bladder. The syringe can then be withdrawn from the patient's urethra, leaving the prosthesis in place. The tube of the prosthesis can be sized such that the material of the shell engages the native urethral tissues to seal the urethra, for example, such that urine does not leak out of the bladder around the tube.

Any of the prostheses described herein can include additional components, which can be remotely-controllable components. As examples, the prostheses described herein can include electronics, microprocessors, RFID devices, sensors, mechanics, magnets, valves, and/or pumps. Such components can be remotely controlled to assist in introducing, deploying, or removing the prosthesis. A patient can use a remote control to actuate these components to empty or evacuate their bladder through the inner flexible conduit 110. A patient can also use a remote control to measure, record, analyze, and/or transmit information regarding their vital signs, including their temperature, heartrate, or blood pressure, or regarding their urinary chemistry, including sodium concentration, cholesterol, etc.

This information can be communicated from the prosthesis within the patient's body to computer systems outside the patient's body, such as by using radio signals, infrared signals, WiFi, Bluetooth, or any other suitable communication technique. A prosthesis can include an RFID device to allow the prosthesis to be detected and/or identified from outside the patient's body, such as by an RFID reader or other suitable device. In some implementations, a metal detector can be used to detect the presence of the prosthesis. Such implementations can help to ensure that the prosthesis is not left in a patient's body at times when doing so would be detrimental, such as if the patient is to undergo an MRI. In some cases, these implementations could allow the patient's body to be identified by the prosthesis or an RFID tag included therein.

To remove the prosthesis, a patient or a physician can simply pull the prosthesis out. The stabilizers can be canted and have a consistent cant so that as the prosthesis is pulled out of a patient's urethra, the prosthesis can also be twisted to help urge the stabilizers to collapse toward or roll into one another into a closed configuration extending in front of the tube to facilitate removal of the prosthesis and to make removal of the prosthesis more comfortable. In cases where a prosthesis is used to capture materials before they enter an inner flexible conduit of the prosthesis, the stabilizers can collapse toward one another and trap such materials between the stabilizers, so that the materials are pulled out of the patient's body as the prosthesis is removed.

Any of the prostheses described herein can be used by male or female patients of any suitable age, such as to help patients suffering from bladder, muscular, or other physical or neurological ailments preventing or complicating normal urination. While the prostheses have been described as urinary prostheses in particular, the technologies described herein can be used in any suitable type of prosthesis. As examples, the technologies described herein can be used to facilitate bowel movements or in a patient's heart valve or ear canal. Further, any of the technologies described herein can be used in various others industries, including fish tanks or aquariums, cars or other vehicles, pipeline or irrigation systems, and gas or liquid pumping systems. Any of the components of the prostheses described herein can comprise any suitable material or materials, such as any suitable plastic, acrylic, metal, mineral, etc.

In some implementations, a funnel (e.g., funnel 104) or stabilizers (e.g., stabilizers 106) of a prosthesis as described herein can be made from a material that is more dense than the material of a piece of tubular material extending through a shell (e.g., shell 108) to form a conduit (e.g., conduit 110), to provide a more rigid structure inside a patient's body. In other implementations, the piece of tubular material extending through the shell can be made from a material that is denser than the material of the funnel and stabilizers to provide a more compliant structure inside the patient's body. In both cases, as noted above, the piece of tubular material extending through the shell can be made of a sufficiently dense or rigid material to prevent collapse of the conduit.

In some embodiments, any one of the prostheses described herein can include one or more propellers or impellers. For example, the prosthesis 100 can include one or more propellers and/or one or more impellers positioned inside the elongate flexible tube 102 and inside the inner flexible conduit 110. In such embodiments, a cable driveline, which can include a flexible braided cable, can be provided for and coupled to each propeller or impeller. The cable driveline(s) can extend through and along the length of the inner flexible conduit, to allow a user to actuate the propellers and/or impellers. The propellers and/or impellers can be actuated to assist in draining a patient's bladder when needed.

Figure 8:
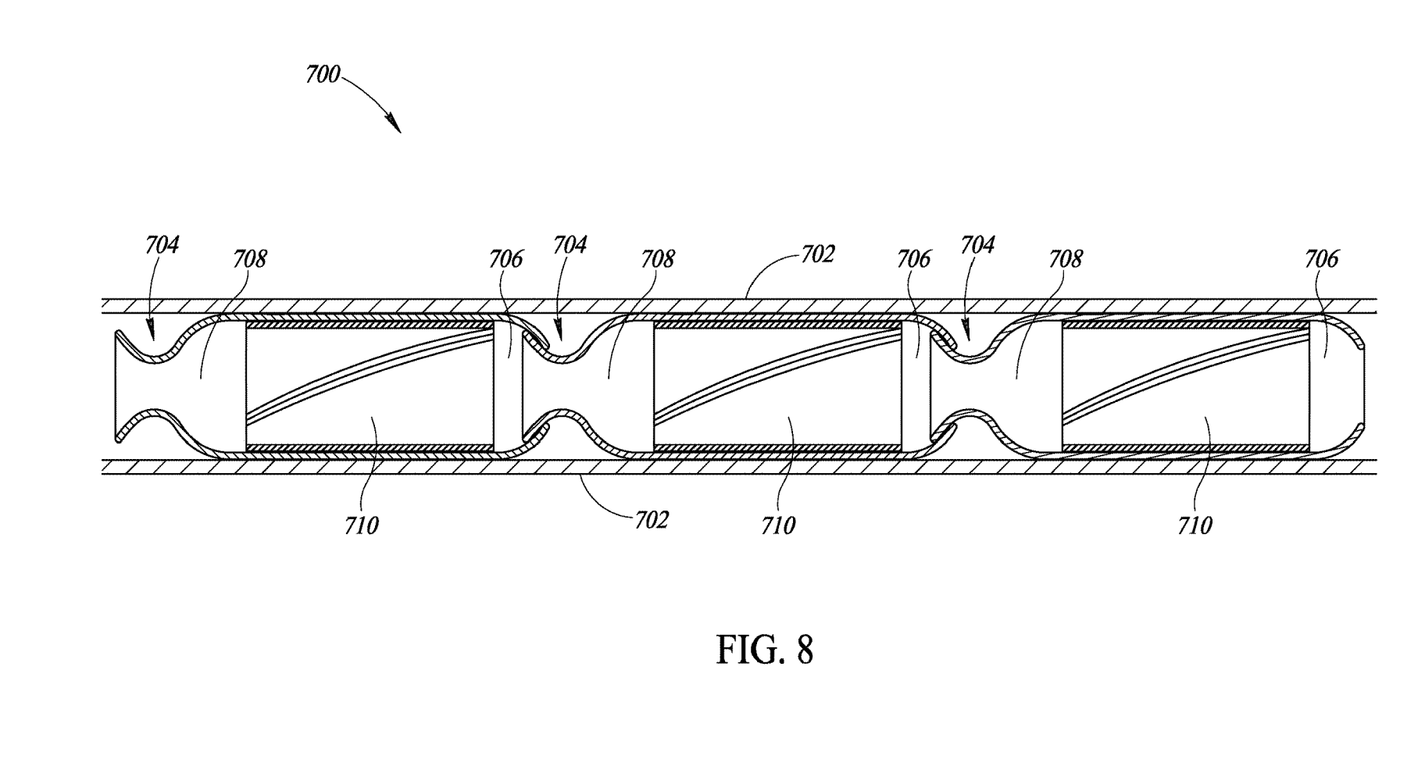
FIG. 8 illustrates a cross-sectional view of another urinary prosthesis, according to yet another embodiment, including a plurality of linked segments.

FIG. 8 illustrates a cross-sectional view of a tubular assembly 700 of a urinary prosthesis or urinary catheter according to yet another embodiment. The tubular assembly 700 includes an outer sheath 702 that can comprise or be coated in a soft pliable silicone or similar material to protect a patient's tissues, provide greater comfort to the patient, and improve the integrity (e.g., the seal, the resilience, and the reliability) of the tubular assembly 700. Inside the outer sheath 702, the tubular assembly 700 includes a plurality of distinct structural segments or links 704. Each of the links 704 has a generally tubular or annular structure and forms a sleeve within which other components can be positioned and through which other objects can pass.

The links 704 are formed from a rigid plastic material to prevent the tubular assembly 700 from collapsing under external pressures. The links 704 are shaped and coupled to one another so that each link 704 can translate, rotate about its central longitudinal axis, and rotate about any axis transverse to its central longitudinal axis, with respect to the adjacent links 704. In particular, each link 704 has a first end portion 706 at which its tubular structure tapers or narrows in diameter at the end of the link 704. Each link 704 also has a second end portion 708, opposite to its first end portion 706, that includes a constriction, or a region that tapers or narrows in diameter and then widens out again at the end of the link 704.

Each of the links 704 can be coupled to two adjacent links by inserting the respective second end portions 708 of the links 704 into the respective first end portions 706 of the adjacent links 704, so that the tapered first end portions 706 surround the respective second end portions 708 and are seated on the second end portions 708 at and within the constrictions of the second end portions 708. By coupling a series of distinct links 704 to one another in this way, the tubular assembly 700 can be flexible and bendable about axes transverse to a central longitudinal axis of the tubular assembly 700, even though the individual links 704 are rigid, to aid in traversing a patient's urethra. In this manner, each link can pitch, yaw, or roll relative to an adjacent link. Further, the curvatures of the first and second end portions 706, 708 of the links 704 can be selected so that they are flush and seal to one another when in use. A length of the tubular assembly 700 can be adjusted by adding or removing individual links 704 until a desired length is achieved.

Figure 9:
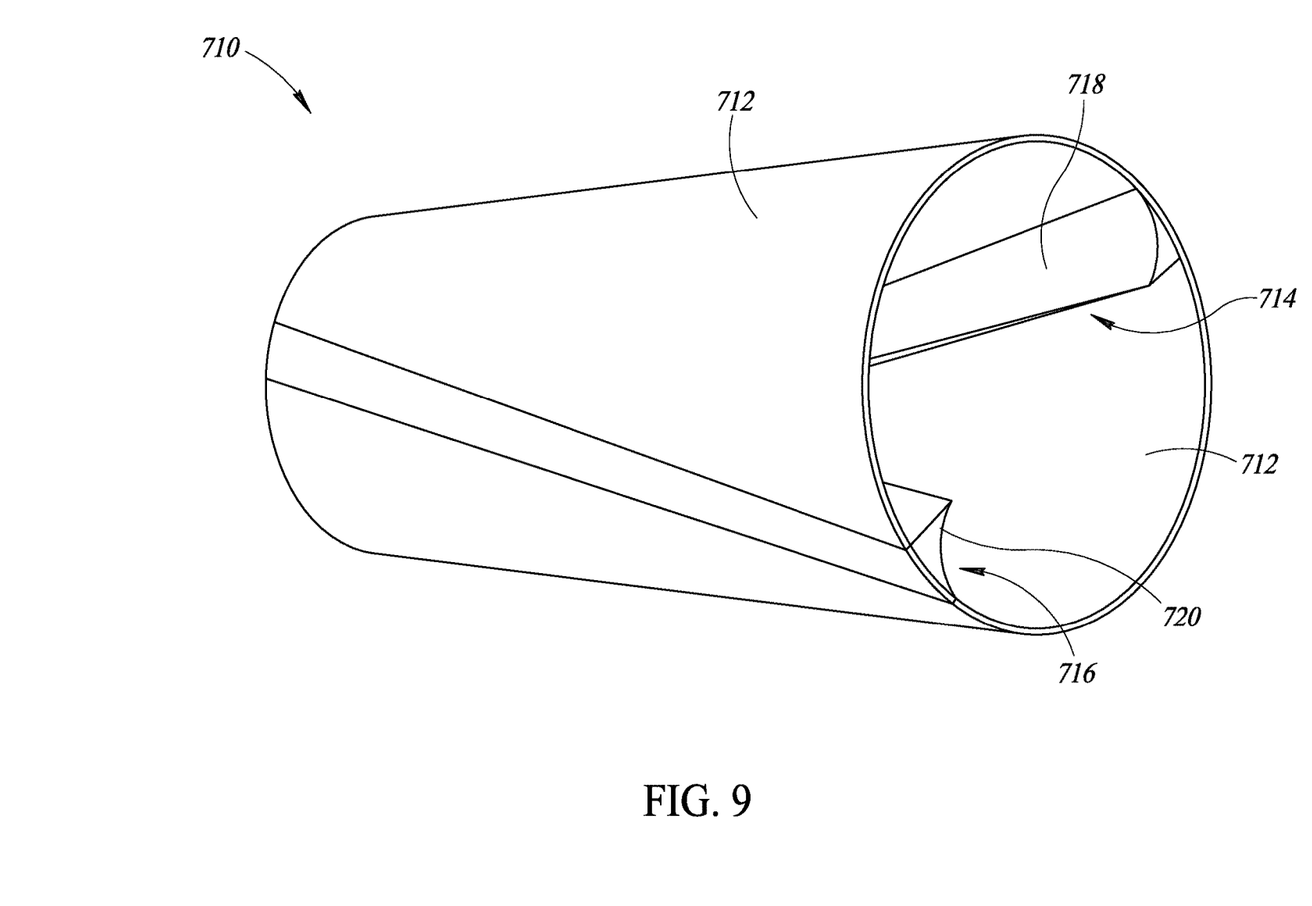
FIG. 9 illustrates a rotatable component of one of the linked segments of the urinary prosthesis of FIG. 8.

As illustrated in FIG. 8, the tubular assembly 700 also includes a respective inner rotating fluid drive unit 710 located within each of the links 704. An example drive unit 710 is illustrated in a perspective view in FIG. 9. As illustrated in FIG. 9, the drive unit 710 includes a hollow, cylindrical body 712 and first and second helical ridges 714, 716, that extend inwardly from an inner surface of the body 712 and longitudinally from a first longitudinal end of the link 704 to a second longitudinal end of the link 704 opposite to the first. The drive unit 710 of the example embodiment shown in FIG. 9 includes two helical ridges, but in alternative embodiments, a drive unit can include 3, 4, 5, 6, or more helical ridges, depending on the specific implementation. The helical shapes of the two ridges 714 and 716 have the same pitch, but in alternative embodiments, can have different pitches. The first and second helical ridges 714, 716, include first and second curved surfaces 718, 720, each having a varying radius of curvature that is configured to improve the ability of the curved surfaces 718, 720 to propel fluid longitudinally through the drive unit 710 as it rotates about its own central longitudinal axis.

The first and second helical ridges 714, 716 comprise magnetic and/or ferromagnetic materials, so that they can interact with magnetic fields induced by other magnetic or ferromagnetic devices located remotely from the tubular assembly 700. For example, the tubular assembly 700 can be positioned in a patient's body, such as within a patient's urethra. A control device that includes one or more electromagnets can be positioned outside of the patient's body and can be used to induce magnetic fields that interact with the first and second helical ridges 714, 716 to cause the drive unit 710 to rotate within the respective link 704 of the tubular assembly 700, and therefore to assist in carrying materials (e.g., fluids such as urine or solids such as kidney stones) out of the patient's bladder through the tubular assembly 700.

Such a control device can operate under computer or algorithmic control to produce or generate the magnetic waves suitable to actuate rotation of the drive unit 710 within the tubular assembly 700. In some cases, suitable magnetic waves include oscillating magnetic waves, wherein the frequency of the oscillation can be increased or decreased to increase or decrease, respectively, the speed of rotation of the drive unit 710 within the tubular assembly 700. In some cases, the frequency of the oscillation of the magnetic waves can be controlled by adjusting a voltage applied to one or more electromagnets creating the magnetic fields.

As described above, a drive unit 710 can be positioned within each of the links 704. In alternative embodiments, a drive unit 710 can be positioned within only specific ones of the links 704. For example, a drive unit 710 can be positioned in every other, or every third one of the links 704. As another example, the tubular assembly 700 can include only a first drive unit 710 positioned within a link 704 at a first end of the tubular assembly 700 and a second drive unit 710 positioned within a link 704 at a second end of the tubular assembly 700 opposite to the first. In each of these cases, multiple drive units 710 can be positioned within respective links 704 and can be spaced apart from one another along the length of the tubular assembly 700.

In some embodiments, multiple drive units 710 within the tubular assembly 700 can be coupled to one another, physically or otherwise, so that they are constrained to rotate in unison with one another within the tubular assembly 700. In other embodiments, all drive units 710 within the tubular assembly 700 can rotate independently of one another within the tubular assembly 700. In cases in which the drive units 710 are independently rotatable with respect to one another, the control device can be used to control any one or any combination of the drive units 710, and in some cases can be used to cause multiple drive units 710 to be synchronized and rotate in unison.

In some cases, the control device can be used to cause the drive units 710 to rotate in a clockwise direction when viewed toward a funnel coupled to an end of the tubular assembly 700, while in other cases the control device can be used to cause the drive units 710 to rotate in a counterclockwise direction when viewed toward a funnel coupled to the end of the tubular assembly 700. It is particularly advantageous to cause the drive units 710 to rotate in the direction of the curved surfaces 718, 720, i.e., such that the curved surfaces 718, 720 lead the rotation of the ridges 714, 716 about the central longitudinal axis of the tubular assembly 700. A lubricant can be positioned between the inner surfaces of the links 704 and the outer surfaces of the drive units 710 to facilitate smooth rotation of the drive units 710 within the tubular assembly 700.

The tubular assembly 700 and its drive units 710, which can be magnetically controlled, is advantageous over other implementations that include a driveline extending through a tube. In particular, omitting a driveline provides additional space within the tubular assembly 700 for other materials to pass through the tubular assembly 700, or allows the overall profile of the tubular assembly 700 to be decreased while maintaining the same space available for other materials to pass through the tubular assembly 700, or both.

U.S. provisional patent application No. 62/237,343, filed Oct. 5, 2015, to which this application claims priority, is hereby incorporated herein by reference in its entirety. Aspects of the various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A urinary prosthesis comprising:
an elongate flexible tube having a central longitudinal axis, the elongate flexible tube including:
an outer sheath;
a plurality of individual links positioned within the outer sheath, each of the individual links including an annular, rigid body, a first one of the links coupled to a second one of the links so that the first one of the links is rotatable about an axis transverse to the central longitudinal axis with respect to the second one of the links; and
a first hollow, cylindrical body that is positioned within the first one of the links and that is rotatable with respect to the first one of the links,
wherein the first individual link includes a first end portion that is tapered, the second individual link includes a second end portion that has a constriction, and the first end portion is seated on and within the constriction of the second end portion.

2. The urinary prosthesis of claim 1 wherein a curvature of the first end portion corresponds to a curvature of the second end portion so that the first end portion is sealed to the second end portion.

3. A urinary prosthesis comprising:
an elongate flexible tube having a central longitudinal axis, the elongate flexible tube including:
an outer sheath,
a plurality of individual links positioned within the outer sheath, each of the individual links including an annular, rigid body, a first one of the links coupled to a second one of the links so that the first one of the links is rotatable about an axis transverse to the central longitudinal axis with respect to the second one of the links; and
a first hollow, cylindrical body that is positioned within the first one of the links and that is rotatable with respect to the first one of the links,
wherein the first hollow cylindrical body includes a first helical ridge extending inwardly from an inner surface of the first hollow cylindrical body and a second helical ridge extending inwardly from the inner surface of the first hollow cylindrical body.

4. The urinary prosthesis of claim 3 wherein the first helical ridge includes a first curved surface having a varying radius of curvature and the second helical ridge includes a second curved surface having a varying radius of curvature.

5. The urinary prosthesis of claim 3 wherein the first and second helical ridges are magnetic or ferromagnetic.

6. A urinary prosthesis comprising:
an elongate flexible tube having a central longitudinal axis, the elongate flexible tube including:
an outer sheath;
a plurality of individual links positioned within the outer sheath, each of the individual links including an annular, rigid body, a first one of the links coupled to a second one of the links so that the first one of the links is rotatable about an axis transverse to the central longitudinal axis with respect to the second one of the links; and
a respective hollow, cylindrical body positioned within and rotatable with respect to each of the plurality of individual links.

7. A urinary prosthesis comprising:
an elongate flexible tube having a central longitudinal axis, the elongate flexible tube including:
an outer sheath;
a plurality of individual links positioned within the outer sheath, each of the individual links including an annular, rigid body, a first one of the links coupled to a second one of the links so that the first one of the links is rotatable about an axis transverse to the central longitudinal axis with respect to the second one of the links;
a first hollow, cylindrical body that is positioned within the first one of the links and that is rotatable with respect to the first one of the links; and
a second hollow, cylindrical body that is positioned within the second one of the links and that is rotatable with respect to the second one of the links.

8. The urinary prosthesis of claim 7 wherein the first hollow cylindrical body is independently rotatable with respect to the second hollow cylindrical body.

9. The urinary prosthesis of claim 7 wherein the first hollow cylindrical body is constrained to rotate in unison with the second hollow cylindrical body.

* * * * *